United States Patent [19]

Trick et al.

[11] Patent Number: 4,698,999
[45] Date of Patent: Oct. 13, 1987

[54] PRESSURE CONNECTOR

[75] Inventors: William A. Trick; Joseph T. Loges, both of Kettering, Ohio

[73] Assignee: General Motors Corporation, Detroit, Mich.

[21] Appl. No.: 891,440

[22] Filed: Jul. 28, 1986

[51] Int. Cl.⁴ ............................................. G01M 3/26
[52] U.S. Cl. ........................................ 73/49.8; 73/40; 73/49.7
[58] Field of Search .................... 73/49.8, 49.7, 40, 39

[56] References Cited

U.S. PATENT DOCUMENTS 3,561,255  2/1971  Kostielney, Jr. ....................... 73/40
4,294,107  10/1981  Walle ............................... 73/49.8 X

FOREIGN PATENT DOCUMENTS 669243  6/1979  U.S.S.R. ............................... 73/49.8
1188557  10/1985  U.S.S.R. ................................. 73/40

*Primary Examiner*—Stewart J. Levy
*Assistant Examiner*—Joseph W. Roskos
*Attorney, Agent, or Firm*—D. D. McGraw

[57] ABSTRACT

A pressure connector is used to temporarily connect a pressure head with a device to be tested under pressure. The pressure head engages a flat surface around an opening and seals against it without any leakage. The pressure head includes a seal head with a seal therein for engaging the flat surface of the device to be tested. The seal head is moveable axially in either direction for a limited distance on an arbor. Suitable compression springs permit the seal head to adapt to slight differences in stroke requirements as the pressure head is used with different parts to be tested. The test pressure, preferably air pressure, is introduced and acts on the seal head and the cup-like seal in the seal head, urging the seal head and the seal into full surface sealing engagement with the flat surface around the opening into which the test pressure is to be introduced into the device being tested. Upon completion of the test pressure step, the mechanism applying a location force to the pressure head arbor for beginning the cycle is removed and the test pressure acting on one end of the arbor moves the arbor to its retracted position. The test pressure is then vented and the device being tested is removed.

4 Claims, 1 Drawing Figure

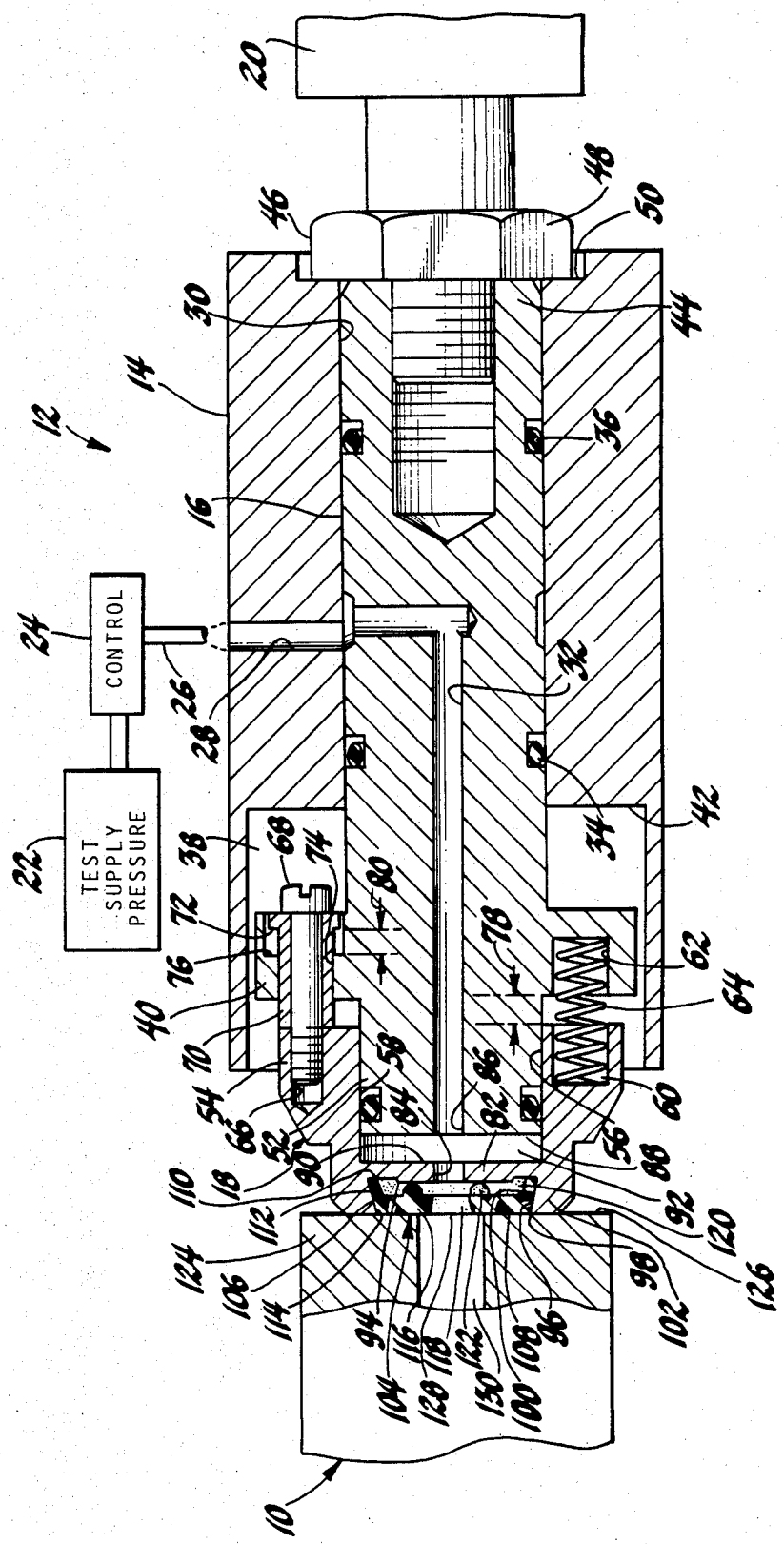

PRESSURE CONNECTOR

The invention relates to a mechanism for pressure connecting two devices while preventing leakage therebetween, and particularly to a temporary pressure connector for use in pressure testing operations.

As production lines have become more automated, it has become desirable to provide testing mechanism which will pressure test the devices being manufactured without pressure leakage and with ready application and removal of the test pressure to the device. For example, it is desirable to test devices such as master cylinders and the like for pressure leaks after they have been assembled. This may be done by applying a desired test pressure fluid to the master cylinder outlets and increasing the test pressure to the desired value. In order to accomplish this, it is also desirable to have the test pressure applied through a seal head for each outlet which seals against a flat surface of the device being tested, and the sealing force is a function of the test pressure being applied so that a sufficient sealing action is always maintained to prevent test fluid leakage while the testing operation is being carried out.

The devices embodying the invention is a pressure head which is attached to a suitable station mechanism so as to be aligned with the devices being tested as each is presented to the station. A plurality of pressure heads embodying the invention may be connected to a plurality of fluid openings of the device to be tested. Similarly, several devices may be concurrently tested by the provision of appropriate pressure heads. A pressure head embodying the invention includes an arbor mounted in a suitable support and axially extending toward the position of the device to be tested. The arbor has a fluid passage therein which is arranged to be controllably connected to a fluid supply which is the source of the desired test pressure. The test fluid is preferably air. The pressure head may be positioned for test purposes and the test pressure applied under suitable controls to the desired value and then released.

The pressure head particularly includes a seal head which is axially resiliently mounted and moveable on one end of the arbor so as to be in sealing engageable relation with a flat surface of the device to be tested. The seal head is also in sealed relation with the arbor. It is axially moveable relative to the arbor to a limited extent and is normally resiliently biased in the direction of the arbor end extending toward the device to be tested. The seal head may be moved axially relative to the arbor in a telescopic manner when the axially exerted force between the pressure head and the device to be tested is sufficient to overcome the axially resilient mounting of the seal head on the arbor. This provides ready axial adjustments for accommodating the pressure head and the device being tested without requiring extreme axial accuracy of placement.

The seal head has a chamber at the end of it, and the chamber has an annular seal mounted therein. The annular seal may be of any suitable material, and is preferably flexible and of a rubber-like material which is able to readily conform to and seal with a facing flat surface on the device to be tested. The annular seal has an outer face surface which engages the flat surface of the device to be tested in surface sealing relation when the seal head is engaged with the device to be tested, therefore sealingly connecting the pressure test fluid passage of the arbor with a suitable fluid pressure opening in the device to be tested, such connection providing for transmission of pressurized test fluid into the device to be tested.

The arbor, the seal head and the seal cooperate to define chambers in the seal head which receive pressurized test fluid from the arbor fluid passage. The pressure test fluid in the chambers act to further urge the seal head into engagement with the flat surface of the device to be tested. It particularly acts on the annular seal to further urge the outer face surface of the annular seal into tighter sealing engagement with the device flat surface with an increasing force as the test pressure of the pressurized test fluid is increased. This operates to maintain a complete seal between the flat surface of the device to be tested and the pressure head while pressurized test fluid pressure is being transmitted between the pressure head and the device being tested.

One of the more specific features of the mechanism embodying the invention is the arrangement wherein the chamber having an end of the arbor as one wall thereof is of larger effective area acted upon by the test pressure to urge the seal head toward engagement with the flat surface of the device to be tested than is the area of the other chamber, also subjected to test pressure, which acts on the annular seal to urge the seal into further sealing engagement with the flat surface of the device to be tested. Therefore the net effect is that the force of the seal acting against the surface of the device to be tested has a reaction force tending to urge the seal head away from the device to be tested which is somewhat less than the action force of the test pressure on the seal head urging the seal head toward the device to be tested. Therefore the force acting on the annular seal and operating to maintain the seal action between the pressure head and the device being tested does not tend to push the seal head away from the device to be tested.

In its broader aspect, the invention is related to a device for transmitting pressurized fluid from a fluid passage in a first member to a fluid passage in a second member, with means sealing the first member relative to the second member while fluid is being transmitted therebetween under pressure. The mechanism embodying the invention is particularly applicable to a temporary pressure connector arrangement of this type.

IN THE DRAWING

The single FIGURE is a somewhat schematic cross-section view, with parts broken away, illustrating the mechanism embodying the invention.

Reference numeral 10 identifies a device to be tested. Such a device may, for example, be a master cylinder or any other suitable fluid pressure mechanism. The pressure head 12 embodies the invention herein disclosed and claimed. Pressure head 12 is illustrated as being mounted in a suitable mount 14 forming a part of a work station at which devices 10 to be tested are presented for test purposes. Pressure head 12 includes an arbor 16 and a seal head 18. The work station has suitable force apply mechanism 20 as well as a source 22 of pressure test fluid available at test pressure. The pressure fluid from source 22 is illustrated as being connected through a suitable pressure control 24 by means of conduit 26 to a passage 28 formed in mount 14. As illustrated, mount 14 has a through bore 30 in which arbor 16 is reciprocably received. Passage 28 is fluid connected to a fluid passage 32 in arbor 16, with seals 34 and 36 being provided on either side of the connection between passages 28 and 32 to prevent leakage of fluid through any portion of bore 30.

Mount 14 has a recess 38 in one end, and arbor 16 has a flange 40 positioned in recess 38 for axial movement therein. The shoulder 42 of the recess is operatively engageable with flange 40 to limit axial movement of the arbor 16 to the right as seen in the drawing. The arbor has an end 44 at the other end of bore 30 from recess 38 which is provided with a bolt or screw 46 threaded into the arbor and having a head 48 engageable with a shoulder 50 to limit movement of the arbor 16 leftwardly in mount 14 as seen in the drawing. A force apply mechanism 20 is illustrated as being engaged axially of the arbor 16 with the screw head 48 so as to apply axial force to the arbor in a leftward direction as seen in the drawing to position the pressure head for test actuation to be further described.

Seal head 18 is reciprocably mounted on the other end 52 of arbor 16. Seal head 18 is a cup-like member with a flange 54 formed about the outer periphery and a recess 56 in which the end 52 of the arbor 16 is sealingly received. A seal 58 provides the appropriate sealing function. Flange 54 has a circumferentially spaced series of recesses 60 which open axially toward the arbor flange 40 and are in axial alignment with similar recesses 62 formed in flange 40. Recesses 60 and 62 have compression springs 64 received therein so that the compression springs will resist axial movement of the seal head 18 to the right relative to arbor 16, as seen in the drawing, and will therefore urge the seal head 18 to the left as seen in the drawing. Flange 54 has additional recesses 66 formed therein in a similar circumferentially spaced manner. It may be desirable, for example, to have recesses 60 and 66 in alternate circumferentially spaced relation. In other instances, a different number of recesses may be provided and therefore the recesses may not so alternate. Recesses 66 are threaded and arranged to receive the threaded ends of guide bolts 68 therein. Guide bolts 68 are each provided with a guide and stop sleeve 70 fitting over the shank of bolt 68 and engaged by the bolt head so that, when the bolt is tightened into recess 66, the sleeve 70 is secured in place, with a sleeve head 72 being positioned adjacent the bolt head 68.

Flange 40 has a set of through holes 74 which are complementary to recesses 66 but of sufficient diameter to slidably receive sleeves 70 therein. The portion of holes 74 opposite seal head 18 are somewhat larger in diameter than the portion in which each sleeve 70 is guided, therefore providing a shoulder abutment 76 cooperating with sleeve head 72 to limit the leftward movement of the sleeve 70, bolt 68, and therefore the seal head 18. In the particular position of the seal head 18 relative to arbor 16 illustrated in the drawing, the springs 64 are partially loaded to axially urge the seal head leftwardly, and are positioned to permit a maximum rightward stroke 78 of the seal head 18 relative to arbor 16 from that position. In this position, sleeve head 72 and abutment 76 are also so positioned that the sleeve head would engage the abutment if the seal head 18 were moved leftward through the additional available stroke distance 80. Thus in the position illustrated, seal head 18 is in an intermediate position between its limits of axial movement relative to arbor 16.

Seal head 18 has a wall 82 forming the bottom of recess 56. Wall 82 has an opening 84 extending axially therethrough which is in axial alignment with the end opening 86 of passage 32 where the passage opens through the end surface 88 of arbor end 52. The wall surface 90 of wall 82 cooperates with the end surface 88 of arbor 16 and a portion of the side wall of recess 56 to define a chamber 92 to which openings 84 and 86 are connected. The other side of wall 82 has a surface 94 which is the bottom of another recess 96 formed in the end of seal head 18. Recess 96 is an inwardly tapered recess in that its opening 98 is of smaller diameter than the diameter of wall surface 94. The peripheral surface 100 of recess 96 is therefore tapered to inwardly increase in diameter. Opening 98 is formed through the end 102 of seal head 18, and that end is illustrated as being an annular end surface. Opening 98 is considerably larger in diameter than opening 84 for reasons to be discussed below.

A seal 104 is mounted in the recess 96. Seal 104 is annular and somewhat cup shaped. Its outer periphery 106 is preferably frusto-conical in shape, tapering from a smaller diameter at its surface 108 to a larger diameter which is substantially the same as the maximum inner diameter of recess 96. The seal outer periphery 106 also extends axially within the recess 96 for substantially the same distance so that the peripheral end 110 of the seal abuts the outer peripheral portion of the wall surface 94 and the seal surface 108 is positioned in the plane of the seal head end 102. The tapered seal surface 112 on the seal outer periphery 106 mates with the tapered surface 114 forming the peripheral wall of recess 96. The main body 116 of seal 104 has an opening 118 formed axially therethrough so that it is in axial alignment with openings 84 and 86. Opening 118 may be frustoconically shaped with the smaller diameter thereof at the chamber or cavity 120, defined by seal 104 and wall 82, and the larger diameter being in the plane of the seal surface 108. The seal main body 116 is provided with a series of protrusions 122, which may be formed as bumps by way of example. They are circumferentially spaced about the seal opening 118 and located radially inward of the seal outer periphery 106. Protrusions 122 extend axially so that they normally engage the surface 94 of wall 82, maintaining the seal main body in the desired space relation to that wall and permitting test fluid to flow into the entire chamber or cavity 120. It can be seen that when test fluid under pressure is in chamber 120, it will act on the seal outer periphery 106 to urge the seal surface 112 into tight sealing relation with the recess tapered surface 114. It will also act on the main body 116 of the seal, urging the main body axially outward. This action cooperates with the device 10 in a manner described below.

The device to be tested may be any suitable fluid pressure device, and may more particularly be a device such as a master cylinder. The device is illustrated as including a boss 124 having a flat surface 126 on the end thereof. An opening 128 formed by a passage 130 in device 10 is located at the flat surface 126. It is to be understood that the device 10 may be constructed without a boss, so long as it has a flat surface 126 and an opening 128 for test fluid pressure introduction into the device and removal therefrom at the completion of the test. Opening 128 may be a pressure outlet from the master cylinder to which a suitable brake conduit is to be connected.

The mechanism embodying the invention is particularly useful as part of an inspection station in a production line for producing master cylinders for example. The mount 14 is suitably positioned relative to equipment moving the devices to be tested into position for a pressure test. In locating the device 10, it is positioned approximately in the correct axially spaced relation to mount 14 so that when the pressure head 12 is actuated and used it will assume approximately the axial position shown in the drawing. When the device 10 is positioned as shown, the force apply mechanism 20 is actuated to apply a force, acting leftward as seen in the drawing, on the arbor 16 through the bolt 46. This force moves the arbor to the position shown. Before the end 102 of the seal head 18 contacts the flat surface 126 of device 10, the seal head 18 is positioned leftwardly on arbor 16 by springs 64 until the abutments 76 are engaged by the sleeve heads 72. The leftward axial movement of arbor 16 brings the end 102 of the seal head 18 into contact with the flat surface 126 of device 10 and the seal head 18 then moves rightwardly relative to the arbor 16, compressing springs 64 until the shoulder 50 of mount 14 is engaged by the bolt head 48, limiting the leftward axial movement of arbor 16. At this time, the seal head 18 is approximately in the axial position shown in relation to arbor 16. Clearly, the distance 78 should not be completely taken up, nor should the distance 80. At this time, not only does end 102 of seal head 18 engage the flat surface 126 of device 10, but the seal surface 108 of seal 104 is also in surface engagement with flat surface 126. The control 24 is then operated to admit test fluid under pressure from the source 22 to the mount passage 28 and the arbor passage 32. The test fluid may be compressed air, although other appropriate test fluids may be used. The pressure in the test fluid passes through opening 86 at the end of passage 32 into chamber 92, through opening 84 into chamber 120, and through opening 118 into the device passage 130. It is then conducted by suitable passages to the various portions of the device 10 which are to be pressure tested. In a typical master cylinder test arrangement, the test pressure may be about 1,000 p.s.i. As the pressure is introduced into chamber 92, it acts on the surface 90 of seal head 18, further urging the seal head leftwardly and therefore urging end 102 thereof into tighter surface engagement with flat surface 126. As the test pressure is introduced in chamber 120, it acts over the effective area of wall surface 94 and also over the effective surface area of the seal 104 so as to urge the seal outer periphery 106 into tight sealing engagement with the tapered surface 114. It also urges the main body 116 of the seal axially toward the flat surface 126. Since it is already in surface contact with that surface, the effect of this urging is the increase in force load from the seal to the flat surface 126, increasing the seal effectiveness. Since the recess 96 is of smaller diameter, even at its maximum, than the diameter of chamber 92, the reaction of the pressure in chamber 120 on wall surface 94 is not sufficient to overcome the force generated by the same pressure value acting on wall surface 90. Therefore the seal head 18 is not urged rightwardly by the pressure which is urging seal 104 into better sealing engagement with flat surface 126. As the test pressure increases to its desired test value, the forces generated by the test pressure also increase so as to continue to provide sufficient sealing engagement force between seal surface 108 and the flat surface 126 of the device 10 being tested. After the test pressure has reached its desired value, an evaluation is made as to the amount of leakage, if any, in the device 10. The force apply mechanism 20 is then actuated to release the force being exerted on arbor 16, and is preferably moved rightwardly relative to the arbor. Since the pressure in chamber 92 is acting on the arbor end surface 88, and operatively reacting through the seal head 18 to the device 10, the force generated by that pressure in chamber 92 will move the arbor rightwardly until the stroke distance 80 is taken up. The test pressure may then be released by operation of the control 24. When the test pressure is air, it may easily be vented to atmosphere so that the passage 32 and chambers 92 and 120 are at atmospheric pressure. Therefore, there will be no forces acting on the seal head 18 generated by that pressure tending to provide an engaging force for engaging the seal head with the device 10. At this point the device 10 may be readily removed from the inspection station. Upon its removal, another device to be tested will be moved in position and the test sequence will be repeated.

The embodiments of the invention in which an exclusive property or privilege is claimed are defined as follows:

1. Mechanism for pressure testing devices such as master cylinders and the like in which each device to be pressure tested has a boss provided with a flat surface and a fluid pressure opening extending through said flat surface, said opening being connected through passage means in said device to portions thereof to be pressure tested by introduction of fluid pressure into said opening at said flat surface, said mechanism comprising:

a pressure head including:
an axially extending arbor having a fluid passage therein and adapted to have test fluid under test pressure selectively introduced therein;
sealing means selectively engaging and sealing said pressure head relative to said boss flat surface while fluid is being transmitted into said fluid pressure opening under pressure, said sealing means comprising:
an axially resiliently mounted and movable seal head mounted on one end of said arbor in sealing relation with said arbor, said seal head having an end which is selectively engageable with said boss flat surface under axially applied force exerted between said pressure head and said device being tested, said seal head being axially movable relative to said arbor in a telescopic manner when the axially exerted force between said device and said pressure head, exerted through said seal head, is sufficient to overcome the axially resilient mounting of said seal head on said arbor;
said seal head having a chamber with an annular seal mounted therein, said annular seal having an outer face surface engaging said boss flat surface in surface sealing relation when said seal head is engaged with said boss flat surface to sealingly connect said arbor fluid passage with said boss fluid pressure opening in pressurized fluid transmitting relation;
said arbor and said seal head and said seal cooperatively defining chamber means receiving pressurized test fluid from said arbor fluid passage with said pressurized test fluid in said chamber means acting to further urge said seal head end into engagement with said boss flat surface and also acting on said annular seal to further urge said seal outer face surface into sealing engagement with said boss flat surface with an increasing force as the test pressure of the pressurized test fluid is increased, thus maintaining a complete seal between said boss flat surface and said pressure head while pressurized test fluid pressure is being transmitted between said pressure head and said device.

2. The mechanism of claim 1, said chamber means defined by said arbor and said seal head and said seal including a first chamber section having one wall thereof formed by the end of said arbor and a second chamber section separated from said first chamber section by a wall of said seal head and connected thereto by an opening through said seal head wall, said second chamber section having another wall thereof formed by said seal, said second chamber section being of smaller diameter than said first chamber section so that the test pressure of pressurized test fluid therein exerts a net force on said seal head urging said seal head toward said boss flat surface, and the test pressure of pressurized test fluid in said second chamber section acting on said seal exerts a force thereon urging said seal into tighter surface sealing engagement with said boss flat surface as the test pressure of pressurized test fluid in said second chamber section increases, maintaining a fluid pressure sealing condition between said boss flat surface and said pressure head sufficient to prevent fluid leakage therebetween while test pressure of pressurized test fluid is being transferred between said pressure head and said device.

3. In a device for transmitting pressurized fluid from a fluid passage in a first member to a fluid passage in a second member, means sealing said first member relative to said second member while fluid is being transmitted therebetween under pressure, said sealing means comprising:

said first member having a resiliently mounted axially movable seal head mounted thereon with said seal head being engageable with said second member under axially exerted force between said members through said seal head, said seal head being movable relative to said first member in a telescopic manner when the axially exerted force between said members exerted through said seal head is sufficient to overcome the resilient mounting of said seal head on said first member;

said seal head having a cavity with an annular seal mounted therein, said annular seal having an outer face surface engaging said second member in surface sealing relation when said seal head is engaged with said second member to sealingly connect said first and second member fluid passages in pressurized fluid transmitting relation, said first member and said seal head and said seal defining chamber means receiving pressurized fluid from said first member fluid passage with said pressurized fluid in said chamber means acting to further urge said seal head into engagement with said second member and also to further urge said seal outer face surface into sealing engagement with said second member with an increasing force as the pressure in the pressurized fluid is increased, thus maintaining a complete seal operatively between said first and second members while pressurized fluid is being transmitted therebetween.

4. A temporary pressure connector adapted to engage a housing flat surface around an opening to be temporarily pressurized, and to pressurize same, said connector comprising:

an axially extending support member movable axially relative to a housing having a flat surface thereon through which an opening to be temporarily presurized extends, said support member having a fluid pressure passage therein opening through one end of said support member and adapted to selectively deliver and remove fluid pressure to said passage one end; a seal head reciprocably and sealingly mounted on said support member and extending over said support member one end and defining therewith a pressure first chamber having a cross-section area substantially equal to the cross-section area of said support member one end; first means connected to said seal head and said support member providing guided limited axial movement of said seal head relative to said support member and second means acting axially between said seal head and a portion of said support member and resiliently urging said seal head axially outward from said support member, thus tending to increase the volume of said first chamber while permitting limited axial movement of said seal head relative to said support member which decreases the volume of said first chamber when force exerted on said seal head overcomes the force of said resiliently urging second means;

said seal head having an end portion axially outwardly spaced from said support member one end and formed with an inwardly flared recess defined in part by an axially tapered circumferentially extending wall and by a transversely extending wall having an opening therethrough connecting said first chamber and said inwardly flared recess, the maximum cross-section area of said inwardly flared recess being at the surface of said transversely extending wall facing said recess and being of less cross-section area than the cross-section area of said first chamber;

and a seal fitted in and mating with said inwardly flared recess axially tapered circumferentially extending wall in sealing relation, said seal having an axially extending opening formed therethrough and an axially facing outer surface positioned axially outwardly of said recess at least to the plane of the extreme outer end of said seal head end portion and adapted to engage the housing flat surface in surface sealing engagement circumferentially surrounding the opening therethrough so that said seal axially extending opening is in fluid communication with the housing opening to be pressurized, said seal further having an axially inner surface cooperating with said transversely extending wall to define therewith a seal pressure second chamber which is continuously fluid connected with said first chamber via said opening in said transversely extending wall, said seal axially inner surface having spaced axially extending means formed thereon and engaging said transversely extending wall to axially locate said seal in said flared recess so that said seal is normally in sealing engagement with said inwardly flared recess axially tapered circumferentially extending wall with fluid access to said second chamber from said first chamber being unimpeded by said seal;

said support member and said seal head being movable axially to engage said seal head and said seal axially facing outer surface with the housing flat surface, after which pressure is provided in said passage means to pressurize said first chamber and act on said seal head to further urge said seal head axially into engagement with the housing flat surface, and to pressurize said second chamber to further urge said seal axially facing outer surface into sealing engagement with the housing flat surface with a force commensurate with the amount of fluid pressure in said second chamber to effectively prevent any fluid pressure leakage between the housing flat surface and the seal, the fluid pressure being delivered through said axial openings in said transversely extending wall of said seal head and said seal to the opening to be pressurized;

said support member and said seal head being axially movable to disengage said seal head and said seal from the housing flat surface after the fluid pressure in said support member passage is released.

* * * * *